(12) United States Patent
Revelant et al.

(10) Patent No.: US 9,873,666 B2
(45) Date of Patent: Jan. 23, 2018

(54) METHOD FOR PREPARING OXYSULPHIDE AND FLUORINATED DERIVATIVES BY SULPHINATION

(71) Applicant: RHODIA OPERATIONS, Paris (FR)

(72) Inventors: Denis Revelant, Genas (FR); François Metz, Irigny (FR); Valery Dambrin, Saint Genis-laval (FR); Marie Chauve, Lyons (FR)

(73) Assignee: RHODIA OPERATIONS, Paris (FR)

( * ) Notice: Subject to any disclaimer, the term of this patent is extended or adjusted under 35 U.S.C. 154(b) by 0 days.

(21) Appl. No.: 15/021,419

(22) PCT Filed: Sep. 11, 2014

(86) PCT No.: PCT/EP2014/069436
§ 371 (c)(1),
(2) Date: Mar. 11, 2016

(87) PCT Pub. No.: WO2015/036504
PCT Pub. Date: Mar. 19, 2015

(65) Prior Publication Data
US 2016/0221939 A1    Aug. 4, 2016

(30) Foreign Application Priority Data
Sep. 12, 2013 (FR) ..................... 13 02126

(51) Int. Cl.
| | | |
|---|---|---|
| C07C 309/00 | (2006.01) |
| C07C 313/04 | (2006.01) |
| C07C 303/32 | (2006.01) |
| B01J 31/02 | (2006.01) |
| C07C 303/02 | (2006.01) |
| C07C 313/02 | (2006.01) |

(52) U.S. Cl.
CPC .......... *C07C 313/04* (2013.01); *B01J 31/0227* (2013.01); *C07C 303/02* (2013.01); *C07C 303/32* (2013.01); *C07C 313/02* (2013.01); *Y02P 20/582* (2015.11)

(58) Field of Classification Search
None
See application file for complete search history.

(56) References Cited

U.S. PATENT DOCUMENTS

| | | |
|---|---|---|
| 5,859,288 A | 1/1999 | Forat et al. |
| 6,203,670 B1 | 3/2001 | Forat et al. |
| 6,737,525 B2 | 5/2004 | Banks et al. |
| 8,404,883 B2 | 3/2013 | Besson |
| 2009/0137840 A1 | 5/2009 | Junk et al. |
| 2009/0216036 A1* | 8/2009 | Besson ............... C07C 313/04 558/61 |
| 2010/0076221 A1 | 3/2010 | Besson |
| 2012/0022269 A1 | 1/2012 | Honda et al. |

FOREIGN PATENT DOCUMENTS

| | | |
|---|---|---|
| CN | 101516836 A | 8/2009 |
| CN | 102153493 A | 8/2011 |
| CN | 102786450 A | 11/2012 |
| EP | 0735023 A1 | 10/1996 |
| FR | 2900403 A1 | 11/2007 |
| WO | 98/05609 A1 | 2/1998 |
| WO | 07/128893 A1 | 11/2007 |

OTHER PUBLICATIONS

Aardahl et al. Applied Spectroscopy, 1996, vol. 50, 71-77.*

* cited by examiner

*Primary Examiner* — Clinton A Brooks
*Assistant Examiner* — Ana Z Muresan

(57) ABSTRACT

The invention concerns a method for preparing an oxysulphide and fluorinated derivative, said method comprising the reacting, in the presence of an organic solvent, of: i) at least one compound of formula Ea-COOR (I), in which Ea represents the fluorine atom or a group having 1 to 10 carbon atoms chosen from fluoroalkyls, perfluoroalkyls and fluoroalkenyls and R represents hydrogen, a monovalent cation or an alkyl group, and ii) a sulphur oxide, said method being such that the initial molar ratio (sulphur oxide/compound of formula (I)) is less than 0.4 and the concentration of sulphur oxide dissolved in the reaction medium is kept constant for the entire duration of the reaction to a value of between 0.2% and 3% by weight by means of continually adding said sulphur oxide to the reaction medium.

17 Claims, No Drawings

METHOD FOR PREPARING OXYSULPHIDE AND FLUORINATED DERIVATIVES BY SULPHINATION

This application is a U.S. national phase entry under 35 U.S.C. §371 of International Application No. PCT/EP2014/069436, filed on Sep. 11, 2014, which claims priority to French Application No. 1302126, filed on Sep. 12, 2013. The entire contents of these applications are explicitly incorporated herein by this reference.

A subject matter of the present invention is an improved process for the preparation of oxysulfide and fluorinated derivatives by a sulfination reaction.

More precisely, the invention relates to the preparation of fluorosulfinic add and its salts, and also of fluoroalkanesulfinic and -sulfonic acids and their salts.

The invention is particularly targeted at the preparation of perfluoroalkanesulfinic and -sulfonic acids and preferably trifluoromethanesulfinic and trifluoromethanesulfonic acids in the salified form.

Perhaloalkanesulfonic acids and more particularly trifluoromethanesulfonic acid are used as catalysts or as intermediates in organic synthesis.

Processes are already known, from EP 0 735 023 and WO 2007/128893, for the synthesis of oxysulfide and fluorinated organic derivatives, in particular of perfluoromethanesulfinic add in the salified form, by reaction of an at least partially salified fluorocarboxylic acid and of a sulfur oxide in a polar organic solvent.

The prior processes require operating with a large amount of sulfur oxide. In point of fact, the high concentration of sulfur oxide promotes competing and consecutive reactions and consequently the production of impurities, which substantially affects the yield of the reaction. Consequently, the prior processes have to be carried out while limiting the degree of conversion in order to prevent excessively great degradation of the desired product.

On continuing its research studies, the applicant company has found that the existing processes could be further improved by controlling the addition of sulfur oxide to the reaction medium in order to keep the concentration of sulfur oxide therein substantially constant while reducing the amount of sulfur oxide involved. The applicant company has thus developed, surprisingly, a novel process for the production of oxysulfide and fluorinated derivatives by a sulfination reaction which results in numerous advantages, in particular the development of a process which is both more environmentally friendly, due to the use of a limited and controlled amount of sulfur oxide, which is a toxic reactant, and more effective, due to a notable improvement in the degree of conversion, in the yield and in the productive output of the process. The consecutive reactions, which are unfavorable, are substantially reduced, which makes it possible to achieve a selectivity of at least 70% while converting virtually all of the starting material (degree of conversion reaching at least 90%), which substantially limits the recyclings of starting material and considerably simplifies the downstream of the process.

A subject matter of the present invention is a process for the preparation of an oxysulfide and fluorinated derivative, comprising the reaction, in the presence of an organic solvent i) of at least one compound of formula Ea-COOR (I), where Ea represents the fluorine atom or a group having from 1 to 10 carbon atoms chosen from fluoroalkyls, perfluoroalkyls and fluoroalkenyls, and R represents hydrogen, a monovalent cation or an alkyl group, and ii) of a sulfur oxide, said process being such that the initial molar ratio (sulfur oxide/compound of formula (I)) is less than 0.4 and the concentration of dissolved sulfur oxide in the reaction medium is kept constant throughout the duration of the reaction at a value of between 0.2 weight % and 3 weight % by a continuous addition of said sulfur oxide to the reaction medium.

In accordance with the invention, the term "reaction medium" is understood to mean the medium in which the chemical sulfination reaction takes place. The reaction medium comprises the reaction solvent and, depending on the progression of the reaction, the reactants and/or the products of the reaction. In addition, it can comprise additives and impurities.

In accordance with the process of the invention, at least one compound of formula Ea-COOR (I) is reacted with a sulfur oxide. Said compound of formula (I) can in particular be a fluorocarboxylic acid (R=H in the formula (I)), a salt of said acid (R=monovalent cation in the formula (I)) or an ester of said add (R=alkyl group in the formula (I) having from 1 to 10 carbon atoms). The process according to the invention results in the preparation of an oxysulfide and fluorinated derivative of formula (II) Ea-SOOR, where R is defined as above. The reaction employed by the process according to the invention is a sulfination reaction.

Preferably, said compound of formula (I) is a salt of a fluorocarboxylic acid in which the R group is a monovalent cation advantageously selected from the group consisting of alkali metal cations, quaternary ammonium cations and quaternary phosphonium cations. Very preferably, it is an alkali metal cation, particularly sodium, potassium, cesium and rubidium, more particularly potassium. Use is preferably made, as quaternary ammonium or phosphonium cations, of tetraalkylammonium or -phosphonium, trialkylbenzylammonium or -phosphonium or tetraarylammonium or -phosphonium cations, the alkyl groups of which, which are identical or different, represent a linear or branched alkyl chain having from 4 to 12 carbon atoms, preferably from 4 to 6 carbon atoms, and the aryl group of which is advantageously a phenyl group. The tetrabutylphosphonium cation is preferably chosen.

In accordance with the invention, the term "fluoroalkyl" is understood to mean a group formed of a linear or branched $C_1$-$C_{10}$ hydrocarbon chain comprising at least one fluorine atom. The term "perfluoroalkyl" is understood to mean a group formed of a linear or branched $C_1$-$C_{10}$ chain comprising only fluorine atoms, in addition to the carbon atoms, and devoid of hydrogen atoms. The term "fluoroalkenyl" is understood to mean a group formed of a linear or branched $C_1$-$C_{10}$ hydrocarbon chain comprising at least one fluorine atom and comprising at least one double bond.

Preferably, the Ea group present in the compound of formula (I) is chosen from the fluorine atom and a group having from 1 to 5 carbon atoms selected from the group consisting of fluoroalkyls, perfluoroalkyls and fluoroalkenyls. Very preferably, the Ea group is selected from the group consisting of the fluorine atom, the $CH_2F$— radical, the $CHF_2$— radical and the $CF_3$— radical. This thus respectively results in the preparation according to the process of the invention of $F$—$SO_2R$, of $CH_2F$—$SO_2R$, of $CHF_2$—$SO_2R$ and of $CF_3$—$SO_2R$, where R is defined as above; preferably, R is an alkali metal cation, very preferably potassium. In particular, the process according to the present invention is a process for the preparation of fluoromethanesulfinic acid in the salified form, of difluoromethanesulfinic acid in the salified form and of trifluoromethanesulfinic acid in the salified form.

In the process of the invention, the compound of formula Ea-COOR (I) which is reacted can be completely or partially a recycled compound which can be obtained, for example, by separation on conclusion of the sulfination reaction or which can originate from a subsequent stage of synthesis, for example during the preparation of a salt of a sulfonimide compound, of a fluorinated compound having a sulfonic acid —$SO_2OH$ functional group or of a fluorinated compound having a sulfonic anhydride functional group.

The process according to the invention is carried out in the presence of sulfur oxide, preferably sulfur dioxide. The sulfur oxide is generally employed in the gaseous form. It can also be introduced in the solution form, in the organic solvent chosen for the reaction, at a concentration generally varying between 1 weight % and 10 weight % and preferably between 3 weight % and 6 weight %.

In accordance with the process of the invention, the initial molar ratio (sulfur oxide/compound of formula (I)) is less than 0.4, preferably less than 0.2. Another essential characteristic of the process of the invention lies in the maintenance of a constant concentration of dissolved sulfur oxide in the reaction medium throughout the duration of the reaction, said concentration being between 0.2 weight % and 3 weight %.

The term "constant concentration" should be understood as meaning, within the meaning of the present invention, that said concentration can vary by ±20%, preferably by ±10%. In accordance with the process of the invention, the monitoring of the concentration of dissolved sulfur oxide, preferably of dissolved sulfur dioxide, in the reaction medium can be provided by an analytical method. The in-line or in situ analysis of the reaction medium is a means which makes it possible to keep the concentration of dissolved sulfur oxide constant. A constant concentration can be maintained by a controlled and continuous addition of sulfur oxide to the reaction medium. The controlled addition of sulfur oxide to the reaction medium, adjusted according to the results provided by the in-line or in situ analysis, advantageously makes it possible to convert the compound of formula (I) into an oxysulfide and fluorinated compound while substantially penalizing the undesired chemistry related to the degradation of the compound of formula (I) by the sulfur oxide, preferably sulfur dioxide.

In accordance with the process of the invention, any analytical method which makes it possible to measure in-line (via a sampling loop) or in situ the concentration of dissolved sulfur oxide, preferably of dissolved sulfur dioxide, in the reaction medium comprising at least one organic solvent as defined below in the present description and a compound of formula (I) is suitable. Preferably, the concentration of dissolved sulfur oxide, preferably of dissolved sulfur dioxide, in the reaction medium is monitored in-line or in situ by Raman spectrometry, by near infrared spectroscopy or by UV spectroscopy. For example, when the concentration of dissolved sulfur oxide in the reaction medium is monitored by Raman spectrometry, the reactor is equipped with a Raman probe which is connected by an optical fiber to the Raman spectrometer, said probe making it possible to monitor, in the medium, the concentration of dissolved sulfur oxide.

The process according to the invention is carried out in the presence of an organic solvent, preferably an aprotic solvent and very advantageously a polar aprotic solvent. Preferably, said solvent comprises very few impurities carrying acidic hydrogen. The term "aprotic solvent" is understood to mean a solvent which, in the Lewis theory, does not have protons to release. Recourse is had, according to the invention, to a solvent which is sufficiently stable under the reaction conditions. It is desirable for the solvent to at least partially, preferably completely, dissolve the compound of formula (I). Thus, the organic solvent is preferably chosen to be polar. It is thus preferable for the polar aprotic solvent which can be used to have a significant dipole moment. Thus, its relative dielectric constant ∈ is advantageously at least equal to approximately 5. Preferably, its dielectric constant is less than or equal to 50 and greater than or equal to 5, and is in particular between 30 and 40. In order to determine if the organic solvent meets the dielectric constant conditions stated above, reference may be made, inter alia, to the tables of the publication: Techniques of Chemistry, II—Organic Solvents—pp. 536 et seq., $3^{rd}$ edition (1970).

In addition, it is preferable for the solvents used in the process of the invention to be capable of indeed solvating the cations, which means that the solvent exhibits certain basicity properties within the Lewis meaning. In order to determine if a solvent satisfies this requirement, its basicity is assessed by referring to the "donor number". A polar organic solvent exhibiting a donor number of greater than 10, preferably of greater than or equal to 20, is chosen. The upper limit does not exhibit any critical nature. Preferably, an organic solvent having a donor number of between 10 and 30 is chosen. It should be recollected that the term "donor number", denoted in abbreviated form DN, gives an indication with regard to the nucleophilic nature of the solvent and reveals its ability to donate its lone pair. The definition of the "donor number" is found in the publication by Christian Reichardt, [Solvents and Solvent Effects in Organic Chemistry—VCH, p. 19 (1990)], where it is defined as the negative ($-\Delta H$) of the enthalpy (kcal/mol) of the interaction between the solvent and antimony pentachloride in a dilute dichloroethane solution.

According to the present invention, as the polar solvent or solvents do not exhibit acidic hydrogen, in particular when the polar nature of the solvent or solvents is obtained by the presence of electron-withdrawing groups, it is desirable for there not to be any hydrogen on the atom in the u position with respect to the electron-withdrawing functional group.

More generally, it is preferable for the pica corresponding to the first acidity of the solvent to be at least equal to approximately 20 ("approximately" emphasizing that only the first figure is significant), advantageously at least equal to approximately 25 and preferably between 25 and 35.

The acidic nature can also be expressed by the acceptor number AN of the solvent, as defined by Christian Reichardt, ["Solvents and Solvent Effects in Organic Chemistry", $2^{nd}$ edition, VCH (RFA), 1990, pages 23-24]. Advantageously, this acceptor number AN is less than 20 and in particular less than 18.

Solvents which satisfy the various requirements and which give good results can in particular be solvents of amide type. Among the amides, amides having a specific nature, such as tetrasubstituted ureas and monosubstituted lactams, are also included. The amides are preferably substituted (disubstituted for the ordinary amides). Mention may be made, for example, of amides, such as N,N-dimethylformamide (DMF), N,N-diethylformamide or N,N-dimethylacetamide, or pyrrolidone derivatives, such as N-methylpyrrolidone. Another particularly advantageous category of solvents is composed of ethers, whether they are symmetrical or asymmetrical and whether they are open or closed. The various glycol ether derivatives, such as the various glymes, for example diglyme, should be incorporated in the category of the ethers. Among the abovementioned solvents, use is preferably made of DMF.

The amount of organic solvent to be employed is determined as a function of the nature of the organic solvent chosen. It is determined so that the concentration of the compound of formula (I) in the organic solvent is preferably between 1% and 40% by weight and more preferably between 5% and 30%.

According to preferred conditions for implementation of the process of the invention, it is desirable to control the content of impurities present in the reaction medium.

The content of labile hydrogen atoms of the system, or more exactly of releasable protons carried by its various components, including their impurities, should be less than the content of fluorinated groups released by the decomposition of the compound of formula (I). The term "labile hydrogen atom" or "releasable proton" is understood to mean a hydrogen atom which is capable of being torn off in the proton form by a strong base. In practice, they are the protons of the acidic functional groups which exhibit a pica of less than approximately 20. The lower the content of releasable protons, the lower the risk of side reactions and the better the yield. The content of releasable protons which are present in the medium is at most equal to 20% of the initial molar concentration of said compound of formula (I). Advantageously, this content is at most equal to 10%, preferably at most equal to 1% (in moles), with respect to the initial content of said compound of formula (I).

The main molecule carrying labile hydrogen atoms is generally water, which is capable of releasing up to two protons per molecule. Generally, it is preferable to use dehydrated reactants and solvents, so that the content by weight of water of each of the reactants is at most equal to 1 per 1000, with respect to the total weight of said reactant. Depending on the combined reaction conditions, such water contents may be satisfactory but, in some cases, it may be advantageous to operate at lower levels, for example of the order of 1 per 10 000. However, it is not necessarily essential to remove all of the water and a water/compound of formula (I) molar ratio of strictly less than 10%, preferably less than 1%, may be tolerated.

Furthermore, it is desirable for the metal impurities to be in small amounts. Metal elements can be present as impurities introduced in particular by the reactants, the solvent or else by the metal equipment as a result of corrosion. Thus, in order not to introduce additional metal contamination, it is important, in particular when the compound of formula (I) is a fluorocarboxylic acid salt, for the latter to be prepared by reaction of a base with the corresponding fluorocarboxylic acid under conditions such that the base is introduced in an amount in the vicinity of ±5% or so and preferably equal to the stoichiometric amount. More generally, it may be indicated that the two categories of metals which may be essentially present, namely transition elements having two valency states (such as copper, iron or chromium) and the elements of column VIII (in particular metals of the platinum column, which is the group consisting of platinum, osmium, iridium, palladium, rhodium and ruthenium), have to be present in the medium at a content, expressed with respect to the fluorocarboxylic acid, at most equal to 1000 molar ppm, preferably at most equal to 10 molar ppm.

In accordance with the process of the invention, the compound of formula (I), preferably the fluorocarboxylic acid in the salified form, the sulfur oxide and the organic solvent are brought into contact. The implementation can be carried out semicontinuously (or semibatchwise) or continuously. Preferably, it is carried out semicontinuously.

According to a semicontinuous implementation, all of the compound of formula (I), preferably the fluorocarboxylic acid salt, can be introduced into the organic solvent and then the sulfur oxide can be continuously added. The sulfur oxide can be introduced in the gaseous form by absorption into the abovementioned medium or else introduced also in solution in an organic solvent, preferably that of the reaction. Advantageously, the sulfur oxide is added after having preheated the solution, formed of the organic solvent and of the compound of formula (I), to a temperature of between 50° C. and 153° C.

According to a continuous embodiment, all of the reactants are introduced continuously. The device where the reaction takes place is generally fed with the compound of formula (I), preferably the fluorocarboxylic acid salt, as a mixture with the organic solvent, and the sulfur oxide is introduced, which reactant can be added to the feed solution comprising the compound of formula (I) and the organic solvent or else can be introduced at different points of the equipment, it being possible for it to be delivered into the headspace of the reactor or into the reaction mass.

Whether carded out semicontinuously or continuously, the process according to the invention preferably comprises the in-line or in situ control of the concentration of dissolved sulfur oxide throughout the duration of the reaction, so as to keep said concentration, in the reaction medium, constant within a range of between 0.2 weight % and 3 weight %.

The process according to the invention is advantageously carried out in equipment which makes possible semicontinuous or continuous implementation. In particular, a perfectly stirred reactor, a cascade of perfectly stirred reactors which are advantageously equipped with a jacket or a tubular reactor equipped with a jacket in which a heat-exchange fluid circulates, the characteristics of which make it possible to achieve the desired reaction temperature, are suitable for the implementation of the process according to the invention.

According to a preferred embodiment of the process according to the invention, silica is introduced into the reaction medium, preferably in an amount such that it represents from 0.1 weight % to 10 weight %, preferably from 0.5 weight % to 10 weight %, in the reaction medium. In particular, the silica is added to the solution formed of the organic solvent and of the compound of formula (I) when the process according to the invention is carried out semicontinuously. The addition of silica makes it possible to substantially reduce the corrosive impact on the reactor of the fluorides generated in the medium by the implementation of the process according to the invention.

In accordance with the process of the invention, the heating of the reaction mixture advantageously takes place at a temperature of between 100° C. and 200° C., preferably between 120° C. and 160° C. The sulfination reaction is advantageously carried out at atmospheric pressure but higher pressures can also be used. Thus, an absolute total pressure chosen between 1 and 20 bar and preferably between 1 and 3 bar may be suitable.

According to another embodiment, the reaction can be carried out at a pressure below atmospheric pressure. The absolute total pressure can be between 1 mbar and 999 mbar, preferably between 500 mbar and 950 mbar and more preferably between 800 mbar and 900 mbar.

The duration of the heating can vary widely as a function of the reaction temperature chosen. It can vary between approximately 30 min and at most one day. It is advantageously from more than one hour to less than 20 hours and more preferably between 2 hours and 7 hours.

According to the continuous embodiment, the mean residence time, which is defined as the ratio of the volume of the reaction mass to the feed flow rate, lies between 30 min and 10 hours and more preferably between 2 hours and 4 hours.

When said sulfur oxide is sulfur dioxide, the resulting mixture from the sulfination stage can comprise two phases: a liquid phase, where a portion at least of the acid Ea-COOH and of the sulfur dioxide are dissolved in said solvent, and a gaseous phase, essentially containing sulfur dioxide and carbon dioxide formed during the reaction.

The progress of the reaction can be monitored by the degree of conversion (DC) of the compound of formula (I), which is the molar ratio of the amount of compound of formula (I) which has disappeared to the initial amount of compound of formula (I) in the reaction medium, this degree being readily calculated after assaying said compound of formula (I) remaining in the medium.

Once the desired degree of conversion has been reached, the reaction mixture can be treated in a way known per se in order to separate the product obtained, it being possible for the starting materials to be recycled in order to produce an additional amount of the targeted oxysulfide and fluorinated derivative. One or more liquid/solid separation operations can be carried out, for example in order to separate possible solid impurities from the reaction medium. The techniques used can be filtration on different types of supports, centrifugation, separation on settling and evaporation, this list not being exhaustive. Alternatively or in addition, one or more liquid/liquid separation operations can be carried out in order to separate and/or purify the product obtained. The techniques used can be distillation, liquid/liquid extraction, separation by reverse osmosis or separation by ion-exchange resins, this list not being exhaustive. These liquid/solid and liquid/liquid separation operations can be carried out under continuous or batchwise conditions, it being possible for a person skilled in the art to choose the most appropriate conditions.

According to one embodiment, the process additionally comprises a stage subsequent to the sulfination reaction which consists in separating the unreacted compound of formula (I) and in recycling this compound in the process.

The oxysulfide and fluorinated derivative prepared according to the process of the invention is advantageously used for the synthesis of a sulfonimide compound $(Ea-SO_2)_2NH$ and of its salts $(Ea-SO_2)_2NMe$ (Me representing an alkali metal), of a fluorinated compound having a sulfonic acid functional group —$SO_2OH$ and exhibiting a formula $Ea-SO_2OH$, or of an anhydride compound of formula $(Ea-SO_2)_2O$, Ea having the definition specified above in the present description.

Another subject matter of the invention is a process for the preparation of a compound selected from the group consisting of a sulfonimide compound $(Ea-SO_2)_2NH$, its salts $(Ea-SO_2)_2NMe$ (Me representing an alkali metal), a fluorinated compound having a sulfonic acid functional group —$SO_2OH$ and exhibiting a formula $Ea-SO_2OH$, and an anhydride compound of formula $(Ea-SO_2)_2O$, Ea having the definition specified above in the present description, said process comprising:
  a stage of preparation of an oxysulfide and fluorinated derivative of formula (II) according to the process described above,
  a stage in which said fluorinated compound of formula (II) is used as reactive compound for the synthesis of a sulfonimide compound $(Ea-SO_2)_2NH$ and of its salts $(Ea-SO_2)_2NMe$ (Me representing an alkali metal), of a fluorinated compound having a sulfonic acid functional group —$SO_2OH$ and exhibiting a formula $Ea-SO_2OH$, or of an anhydride compound of formula $(Ea-SO_2)_2O$, Ea having the definition specified above in the present description.

Another subject matter of the invention is thus a process for the preparation of a salt of a sulfonimide compound of formula $(Ea-SO_2)_2NMe$ from an oxysulfide and fluorinated derivative of formula (II) comprising:
  a) the preparation of an oxysulfide and fluorinated derivative of formula (II) according to the process described above;
  b) a stage of oxidation, for example by chlorination, in order to obtain the compound $(Ea-SO_2)X$, where X is chlorine or fluorine;
  c) a stage of ammonolysis of $Ea-SO_2X$ to give $(Ea-SO_2)_2N.HNR''_3$;
  d) a stage of acidification of $(Ea-SO_2)_2N.HNR''_3$ to give $(Ea-SO_2)_2NH$;
  e) a stage of neutralization, by an alkali metal base, of $(Ea-SO_2)_2NH$ to give $(Ea-SO_2)_2NMe$; and
  f) optionally a stage of drying $(Ea-SO_2)_2NMe$;

In which Ea is defined as above, R" represents a linear or branched alkyl group having from 1 to 20 carbon atoms and Me represents an alkali metal. Preferably, Me is lithium. Stages c), d), e) and f) are known to a person skilled in the art. In particular, the ammonolysis stage is described in the U.S. Pat. No. 5,723,664. The oxidation, acidification, neutralization and drying stages are conventional stages which can be carried out under the conditions known to a person skilled in the art.

Specifically, the present invention can also have, as subject matter, the linking together of the stages (a) and (b) described above. Thus, the invention relates to a process for the preparation of a compound $Ea-SO_2X$, where X is chlorine or fluorine, comprising:
  a) the preparation of an oxysulfide and fluorinated derivative of formula (II) according to the process described above;
  b) a stage of oxidation, for example by chlorination, in order to obtain the compound $Ea-SO_2X$, where X is chlorine or fluorine.

Preferably, the oxysulfide and fluorinated derivative of formula (II) is a trifluoromethylsulfinate alkali metal salt, so that it can be used in the synthesis of bis(trifluoromethanesulfonyl)imide of formula $(CF_3SO_2)_2NH$ and of lithium bis(trifluoromethanesulfonyl)imide of formula $(CF_3SO)_2NLi$ (LiTFSI).

More preferably, the oxysulfide and fluorinated derivative of formula (II) exhibits the formula F—$SO_2$—R, where R is defined as above (R=H, monovalent cation or alkyl group), so that it can be used in the synthesis of bis(fluorosulfonyl)imide of formula $(F—SO_2)_2NH$ and of lithium bis(fluorosulfonyl)imide of formula $(F—SO_2)_2NLi$ (LiFSI).

The sulfonimide compounds and their salts prepared according to the processes described above can advantageously be used as electrolyte salts, as antistatic agent precursors or as surfactant precursors. In particular, said compounds can advantageously be used as electrolytes in the manufacture of batteries, in the fields of electrochromism, electronics and electrochemistry. They are advantageously employed as antistatic agents in the manufacture of pressure-sensitive adhesives (PSAs). As antistatic agents, they can also be employed as components of lubricants. They are used in optical materials, such as electroluminescent devices, and participate in the composition of photovoltaic panels. These uses are also subject matters of the invention. In particular, a subject matter of the invention is a process for the manufacture of an electrochemical device, preferably a battery, said process comprising a stage of preparation of a sulfonimide compound or of its salts according to the process described above and a stage of manufacture of the electrochemical device in which the sulfonimide compound or its salts is employed as electrolyte.

The oxysulfide and fluorinated derivative of formula (II) prepared according to the process of the invention is also advantageously used in the preparation, by oxidation, of a fluorinated compound of formula $Ea-SO_2$—OH where Ea is defined as above. To this end, said oxysulfide and fluorinated derivative of formula (II) resulting from the process of the invention is, for example, brought together with an aqueous alkaline solution and then an acidification stage is carried out in order to release the compound $Ea-SO_2$—OH, for example by using a solution of a strong inorganic acid, such as sulfuric acid or hydrochloric acid. Another subject matter of the present invention is thus a process for the preparation of a fluorinated compound of formula $Ea-SO_2$—OH from an oxysulfide and fluorinated derivative of formula (II) comprising:
- a) the preparation of an oxysulfide and fluorinated derivative of formula (II) according to the process described above;
- b') the oxidation of the oxysulfide and fluorinated derivative of formula (II) in order to obtain a fluorinated compound of formula $Ea-SO_2$—OH, where Ea is defined as above.

Preferably, the oxysulfide and fluorinated derivative of formula (II) is a trifluoromethylsulfinate alkali metal salt ($CF_3SO_2R$, where R is an alkali metal), so that it can be used in the synthesis of trifluoromethanesulfonic acid (known as triflic acid) of formula $CF_3SO_2OH$.

The compound $Ea-SO_2$—OH thus obtained is advantageously converted into an anhydride of formula $(Ea-SO_2)_2O$. The anhydrization reaction is known to a person skilled in the art and is described in particular in the U.S. Pat. No. 8,222,450. Preferably, the oxysulfide and fluorinated derivative of formula (II) is a trifluoromethylsulfinate alkali metal salt, so that the anhydrization of the triflic acid results in the production of trifluoromethanesulfonic anhydride of formula $(CF_3SO_2)_2O$. Another subject matter of the present invention is a process for the preparation of an anhydride compound of formula $(Ea-SO_2)_2O$, where Ea is defined as above, from an oxysulfide and fluorinated derivative of formula (II), comprising:
- a) the preparation of an oxysulfide and fluorinated derivative of formula (II) according to the process described above;
- b') the oxidation of the oxysulfide and fluorinated derivative of formula (II) in order to obtain a fluorinated compound of formula $Ea-SO_2$—OH;
- c') the anhydrization of the fluorinated compound of formula $Ea-SO_2$—OH in order to obtain an anhydride compound of formula $(Ea-SO_2)_2O$.

The fluorinated compounds of formula $Ea-SO_2$—OH and the anhydride compounds of formula $(Ea-SO_2)_2O$ can be used in various applications, in particular as acid catalyst, as protective group in organic synthesis, as synthon in the fields of pharmaceuticals, agrochemistry or electronics, or as salt for the electronics industry.

The examples which follow illustrate the invention without, however, limiting it.

The degree of conversion (DC) corresponds to the ratio of the number of moles of substrate converted to the number of moles of substrate employed.

The reaction yield (RY) corresponds to the ratio of the number of moles of product formed to the number of moles of substrate employed.

EXAMPLE 1 (COMPARATIVE)

Preparation of Potassium Trifluoromethylsulfinate $CF_3SO_2K$ by Sulfination of Potassium Trifluoroacetate in the Presence of $SO_2$ According to a Batch Implementation 125.5 g of dimethylformamide are charged, at ambient temperature (approximately 20° C.), to a 500 cm³ reactor provided with a jacket, with a central mechanical stirrer and with outlet to the atmosphere and with an acetone/dry ice condenser which makes possible the reflux of the sulfur dioxide. 25.5 g of potassium trifluoroacetate are introduced into the DMF. 6.9 g of sulfur dioxide are subsequently charged via a capillary connected to a pressurized sulfur dioxide cylinder. Heating is carried out to 140° C. at atmospheric pressure. The $SO_2$/KTFA molar ratio is equal to 0.64.

After 4 hours 25 minutes, ion chromatographic analysis gives the following results:
Degree of conversion of the potassium trifluoroacetate: 57.1%
Yield of potassium trifluoromethylsulfinate: 52.8%

EXAMPLE 2 (INVENTION)

Preparation of Potassium Trifluoromethylsulfinate $CF_3SO_2K$ by Sulfination of Potassium Trifluoroacetate in the Presence of $SO_2$ According to a Semicontinuous Implementation The following are introduced at ambient temperature into a 500 ml jacketed reactor equipped with a condenser having an aqueous glycol solution at −15° C., with a stirrer and with baffles:
200 g of anhydrous dimethylformamide (DMF)
50 g of potassium trifluoroacetate (KTFA), i.e., a KTFA concentration equal to 20 weight % in the DMF-KTFA mixture.

The reactor is equipped with a Raman probe which makes it possible to monitor, in the medium, the concentration of dissolved $SO_2$; this probe is connected by an optical fiber to the Raman spectrometer.

The medium is stirred and brought to a temperature of 100° C.

Via a dip pipe connected to the $SO_2$ cylinder, an amount of 1.25 g of gaseous $SO_2$ is continuously introduced into the reactor through a micrometric regulating valve, so as to have a concentration of dissolved $SO_2$ equal to 0.5 weight % and an initial $SO_2$/KTFA molar ratio of 0.059.

The temperature is brought to 145° C. while keeping the $SO_2$ concentration constant at 0.5 weight %. The reaction is allowed to take place for 5 hours while regulating the $SO_2$ concentration at 0.5 weight %.

After 5 hours, the reaction mixture is cooled and analyzed by NMR, and the results are as follows:
Degree of conversion of the potassium trifluoroacetate: 90%
Yield of potassium trifluoromethylsulfinate: 64.8%

A marked improvement in the reaction yield and conversion is observed.

The invention claimed is:

1. A process for the preparation of an oxysulfide and fluorinated derivative, comprising the reaction, in the presence of an organic solvent, of:
   i) at least one compound of formula Ea-COOR (I), wherein Ea represents a fluorine atom or a group having from 1 to 10 carbon atoms selected from the group consisting of fluoroalkyls, perfluoroalkyls and fluoroalkenyls, and R represents hydrogen, a monovalent cation or an alkyl group, and
   ii) a sulfur oxide, wherein the initial sulfur oxide/compound of formula (I) molar ratio is less than 0.4 and the concentration of dissolved sulfur oxide in the reaction medium is kept constant throughout the duration of the reaction at a value of between 0.2 weight % and 3 weight % by a continuous addition of said sulfur oxide to the reaction medium.

2. The process according to claim 1, wherein the compound of formula (I) is a salt of a fluorocarboxylic acid in which the R group is a monovalent cation selected from the group consisting of alkali metal cations, quaternary ammonium cations and quaternary phosphonium cations.

3. The process according to claim 2, wherein R is an alkali metal cation.

4. The process according to claim 1, wherein the Ea group is selected from the group consisting of a fluorine atom, a $CH_2F$— radical, a $CHF_2$— radical and a $CF_3$— radical.

5. The process according to claim 1, wherein the sulfur oxide is sulfur dioxide.

6. The process according to claim 1, wherein the initial sulfur oxide/compound of formula (I) molar ratio is less than 0.2.

7. The process according to claim 1, wherein the concentration of dissolved sulfur oxide in the reaction medium is monitored in line or in situ by Raman spectrometry, by near infrared spectroscopy or by UV spectroscopy.

8. The process according to claim 1, wherein the organic solvent is a polar aprotic solvent.

9. The process according to claim 8, wherein the solvent is N,N-dimethylformamide (DMF), N,N-diethylformamide or N,N-dimethylacetamide.

10. The process according to claim 1, wherein the concentration of the compound of formula (I) in the organic solvent is between 1 weight % and 40 weight %.

11. The process according to claim 1, wherein the process is carried out continuously or semicontinuously.

12. The process according to claim 1, wherein the reaction is carried out at an absolute total pressure between 1 and 20 bar.

13. The process according to claim 1, wherein the reaction is carried out at a pressure below atmospheric pressure.

14. A process for the preparation of a compound selected from the group consisting of a sulfonimide compound $(Ea-SO_2)_2NH$, its salts $(Ea-SO_2)_2NMe$, Me representing an alkali metal, a fluorinated compound having a sulfonic acid functional group —$SO_2OH$ and exhibiting a formula $Ea-SO_2OH$, and an anhydride compound of formula $(Ea-SO_2)_2O$, wherein Ea represents a fluorine atom or a group having from 1 to 10 carbon atoms selected from the group consisting of fluoroalkyls, perfluoroalkyls and fluoroalkenyls, said process comprising:
   preparation of an oxysulfide and fluorinated derivative according to the process of claim 1,
   using the oxysulfide and fluorinated compound as reactive compound for the synthesis of a sulfonimide compound $(Ea-SO_2)_2NH$ and of its salts $(Ea-SO_2)_2NMe$, Me representing an alkali metal, of a fluorinated compound having a sulfonic acid functional group —$SO_2OH$ and exhibiting a formula $Ea-SO_2OH$, or of an anhydride compound of formula $(Ea-SO_2)_2O$.

15. The process according to claim 14, wherein the salt of a sulfonimide compound of formula $(Ea-SO_2)_2NMe$ is prepared from the oxysulfide and fluorinated derivative the process comprising:
   a) the preparation of the oxysulfide and fluorinated derivative;
   b) oxidation of the oxysulfide and fluorinated derivative in order to obtain the compound $(Ea-SO_2)X$, where X is chlorine or fluorine;
   c) ammonolysis of $Ea-SO_2X$ to give $(Ea-SO_2)_2N.HNR''_3$;
   d) acidification of $(Ea-SO_2)_2N.HNR''_3$ to give $(Ea-SO_2)_2NH$;
   e) neutralization, by an alkali metal base, of $(Ea-SO_2)_2NH$ to give $(Ea-SO_2)_2NMe$; and
   f) optionally drying $(Ea-SO_2)_2NMe$;
wherein R" represents a linear or branched alkyl group having from 1 to 20 carbon atoms and Me represents an alkali metal.

16. The process according to claim 14, wherein the fluorinated compound of formula $Ea-SO_2$—OH is prepared from the oxysulfide and fluorinated derivative the process comprising:
   a) the preparation of the oxysulfide and fluorinated derivative;
   b') the oxidation of the oxysulfide and fluorinated derivative in order to obtain the fluorinated compound of formula $Ea-SO_2$—OH.

17. The process according to claim 14, wherein the anhydride compound of formula $(Ea-SO_2)_2O$ is prepared from the oxysulfide and fluorinated derivative the process comprising:
   a) the preparation of the oxysulfide and fluorinated derivative;
   b') the oxidation of the oxysulfide and fluorinated derivative in order to obtain a fluorinated compound of formula $Ea-SO_2$—OH;
   c') the anhydrization of the fluorinated compound of formula $Ea-SO_2$—OH in order to obtain an anhydride compound of formula $(Ea-SO_2)_2O$.

* * * * *